United States Patent [19]

Sonoi et al.

[11] Patent Number: 4,885,398

[45] Date of Patent: Dec. 5, 1989

[54] PROCESS FOR PRODUCING HEXAFLUOROACETONE OR ITS HYDRATE

[75] Inventors: Takehiro Sonoi, Ohtsu; Toshimasa Sagawa, Nakago; Okimasa Yamada, Isohara; Tetsuya Mizuno, Kitaibaraki, all of Japan

[73] Assignee: Nippon Mektron Limited, Tokyo, Japan

[21] Appl. No.: 189,034

[22] Filed: May 2, 1988

[51] Int. Cl.$^4$ .............................................. C07C 45/40
[52] U.S. Cl. ..................................... 568/404; 568/399
[58] Field of Search ..................... 568/385, 404, 322

[56] References Cited

U.S. PATENT DOCUMENTS

| | | | |
|---|---|---|---|
| 3,321,515 | 5/1967 | Moore et al. | 568/419 |
| 4,067,884 | 1/1978 | Martini | 568/404 |
| 4,337,361 | 6/1982 | Anello et al. | 568/419 |

FOREIGN PATENT DOCUMENTS

| | | | |
|---|---|---|---|
| 618346 | 4/1961 | Canada | 568/404 |
| 40-27173 | 9/1962 | Japan | 568/385 |
| 61-277645 | 12/1986 | Japan | 568/419 |

OTHER PUBLICATIONS

Canadian Journal of Chemistry—vol. 33, Mar. 1955, No. 3, "Organic Fluorine Compounds".

*Primary Examiner*—James H. Reamer
*Attorney, Agent, or Firm*—Fred Philpitt

[57] ABSTRACT

Hexafluoracetone or its hydrate is produced in a higher yield than that of the conventional process (1) by oxidizing a heptafluoroisobutenyl ether with ozone or (2) by thermally decomposing an octafluoroisobutyl ether or a heptafluoroisobutenyl ether in the presence of oxygen and an activated carbon catalyst.

4 Claims, No Drawings

PROCESS FOR PRODUCING HEXAFLUOROACETONE OR ITS HYDRATE

BACKGROUND OF THE INVENTION

1. Field of the Invention

This invention relates to a process for producing hexafluoroacetone or its hydrate, and more particularly to a process for producing hexafluoroacetone or its hydrate with effective utilization of octafluoroisobutene or its adduct with alcohol etc.

2. Description of the Prior Art

Hexafluoroacetone is a monomer for producing a synthetic resin, a synthetic rubber, etc., or is used as an intermediate for crosslinking agents such as bisphenol AF, etc., or as an intermediate raw material for medicaments, agricultural chemicals, etc.

The following processes have been so far proposed for producing hexafluoroacetone or its hydrate having the said applications.

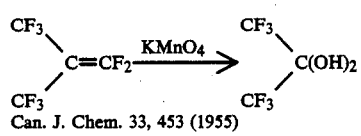
Can. J. Chem. 33, 453 (1955)

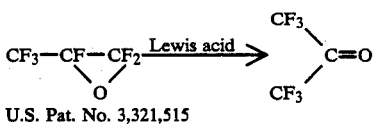
U.S. Pat. No. 3,321,515

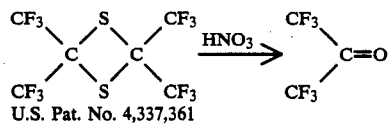
U.S. Pat. No. 4,337,361

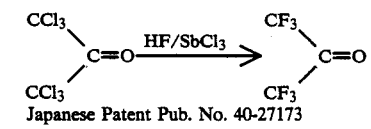
Japanese Patent Pub. No. 40-27173

However, the foregoing processes have the following disadvantages.

(1) Oxidation reaction by potassium permanganate proceeds vigorously and the by-produced manganese dioxide is an industrial waste which is hard to treat.

(2) High purity oxide is hard to synthesize from hexafluoropropene and thus the produced hexafluoroacetone contains hexafluoropropene, etc.

(3) In the oxidation of hexafluorothioacetone dimer by nitric acid, the produced hexafluoroacetone hydrate contains $NO_2$ and $SO_2$, whose removed is troublesome.

(4) In the use of hexachloroacetone, chlorine not only contributes to increase the weight, but also is synthetically not efficient, and furthermore toxic antimony pentachloride is required. Thus, a high purity product is hard to obtain.

Besides the foregoing prior art, a process for producing hexafluoroacetone or its hydrate by reaction of heptafluoroisobutenyl alkyl ether with oxygen under light irradiation has been proposed by the present Applicant [Japanese Patent Application Kokai (Laid-open) No. 61-277,645], but the yield on the basis of raw material heptafluoroisobutenyl alkyl ether is as low level as 19.2 to 19.4%.

SUMMARY OF THE INVENTION

An object of the present invention is to provide a process for producing hexafluoroacetone or its hydrate more advantageously than the conventional process based on oxidation by potassium permanganate, by-producing manganese dioxide or the process based on oxidation by expensive periodic acid.

Another object of the present invention is to effectively utilize octafluoroisobutene or its adduct with alcohol etc.

Further object of the present invention is to improve the yield of hexafluoroacetone or its hydrate when produced from octafluoroisobutyl ether or heptafluoroisobutenyl ether as a raw material.

DETAILED DESCRIPTION OF THE PREFERRED EMBODIMENTS

These objects of the present invention can be attained by producing hexafluoroacetone or its hydrate according to one of the following processes:

(1) a process for oxidizing a heptafluoroisobutenyl alkyl, aryl or benzyl ether with ozone, (2) a process for thermally decomposing an octafluoroisobutyl alkyl, aryl or benzyl ether at a temperature of 50° to 600° C. in the presence of oxygen and an activated carbon catalyst, and (3) a process for thermally decomposing a heptafluoroisobutenyl alkyl, aryl or benzyl ether at a temperature of 50° to 600° C. in the presence of oxygen and an activated carbon catalyst.

Octafluoroisobutene as the starting material is a by-product from the production of hexafluoropropane as one of the important raw materials for fluorine-containing copolymers. Generally, this highly toxic octafluoroisobutene is readily capable of forming octafluoroisobutyl alkyl ethers as alcohol adducts with lower alcohols, such as methanol, ethanol, n-propanol, isopropanol, n-butanol, etc. Likewise, aryl ethers or benzyl ether are formed as adducts of phenols or adduct of benzyl alcohol.

The octafluoroisobutyl ethers are dehydrofluorated with a hydroxide or carbonate of an alkali metal or alkaline earth metal or a base such as a trialkylamine with stirring in the presence of an interphase transfer catalyst such as a quaternary ammonium salt, etc., whereby the corresponding heptafluoroisobutenyl alkyl, aryl or benzyl ether can be obtained.

According to the process (1), oxidation of the heptafluoroisobutenyl alkyl, aryl or benzyl ether with ozone is carried out. In the oxidation with ozone, heptafluoroisobutenyl alkyl, aryl or benzyl ether is charged into a glass reactor vessel, and bubbled with an ozone-containing oxygen or air by an ozone generator of silent discharge type in the absence of a solvent or in the presence of a solvent such as hydrocarbon, halogenated hydrocarbon, ether, water or the like with vigorous stirring.

In the oxidation, hexafluoroacetone (HFA) or its hydrate seems to be synthesized through an ozonide compound, as given by the following equations:

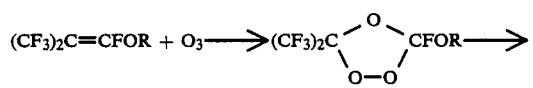

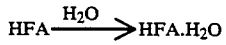

where R is an alkyl group of $C_1$ to $C_{10}$, aryl group or benzyl group.

The ozone is used in the oxidation at a concentration of about 2.5 to about 400 mg per l of oxygen or air and in a molar ratio of about 1 to the heptafluoroisobutenyl alkyl, aryl or benzyl ether. The oxidation temperature is usually −70° to 110° C., preferably −40° to 60° C.

After the oxidation, the reaction mixture is usually successively led to a water trap and a dry ice-methanol trap to recover the product. From the water trap, hexafluoroacetone is obtained as a hydrate. The thus obtained hydrate itself of hexafluoroacetone can be used as a solvent for polyester, polyamide, etc., and can be also dehydrated with phosphorus pentoxide, concentrated sulfuric acid, sulfuric anhydride, or molecular sieves [Japanese Patent Applications Kokai (Laid-open) Nos. 57-81,433 and 59-157,045].

Formation of hexafluoroacetone in the decomposition gas obtained by the oxidation with ozone can be detected by GLS analysis, but owing to the existence of other by-product gases in the decomposition gas, the decomposition gas is once introduced into water to make and separate the hydrate of hexafluoroacetaone without direct separation of hexafluoroacetone. This procedure is very simple and convenient.

The oxidation with ozone has a yield of 22.5% on the basis of heptafluoroisobutenyl alkyl ether and a yield of 69.7% on the basis of the introduced ozone. The former yield is considerably better than that obtained by oxidation with oxygen under the irradiation of ultraviolet rays as disclosed in said Japanese Patent Application Kokai (Lain-open) No. 61-277,645.

In said processes (2) and (3), either octafluoroisobutyl ether or heptafluoroisobutenyl ether derived therefrom can be used as the raw material, whereas in the process previously proposed by the Applicant, that is, the process for producing hexafluoroacetone or its hydrate by reaction of heptafluoroisobutenyl ether with oxygen under the irradiation of light (Japanese Patent Application Kokai (Laid-open) No. 61-277,645], only heptafluoroisobutenyl ether can be used as the raw material and octafluoroisobutenyl ether cannot be used as the raw material.

Thermal decomposition reaction of these raw materials can be carried out by passing the raw material together with oxygen or an oxygen-containing gas in a molar ratio of the oxygen to the raw material of about 1 to about 2 through a metallic reactor tube filled with an activated carbon catalyst under the atmosphenic pressure or a superatmospheric pressure.

The activated carbon for use as the catalyst can be in any shape such as a powdery form, a granular form, a pellet form, a honeycomb form, a bar form, a cylindrical form, etc., and particularly it is desirable to use an activated carbon catalyst in a granular form having a specific surface area of about 1 to about 300 m$^2$/g, preferably about 20 to about 200 m$^2$/g.

The reaction in the presence of such an activated carbon catalyst is carried out at a temperature of about 50° to about 600° C., preferably about 150° to about 300° C. Below about 50° C., the thermal decomposition rate is too low and a lower temperature is not preferable from the pointview of economy and efficiency, whereas above about 600° C. the energy cost is increased and the deterioration of the reactor material is accelerated, and thus a higher temperature is not preferable.

Recovery and dehydration of hexafluoroacetone hydrate after the oxidation can be carried out in the same manner as in the process (1).

The oxidation in the presence of such an activated carbon catalyst has a yield of about 29 to about 30% on the basis of the raw material, which is higher than obtained in the process (1).

PREFERRED EMBODIMENTS OF THE INVENTION

The present invention will be described in detail below, referring to Examples.

EXAMPLE 1

200 g (0.88 moles) of heptafluoroisobutenyl methyl ether (purity: 93%) was charged into a flask having a capacity of 300 ml, provided with a Dimroth condenser, a stirrer and a gas inlet, and about 504 l of ozone-containing oxygen at an ozone concentration of 27.1 mg/l was bubbled into the charged heptafluoroisobutenyl methyl ether at the temperature of 25° C. with vigorous stirring for 16.8 hours. The off-gas was introduced into 1.5 l of water in another flask and further into 500 ml of dry ice-methanol trap, and then discharged.

About 2.5% by weight of hexafluoroacetone hydrate was formed in the water trap (1459 g), as determined according to the F-NMR internal standard method, and extracted and separated with an etheral solvent. From the reactor flask and the dry ice-methanol trap, 30.5 g and 134.2 g of the raw material were recovered, respectively.

Yield based on the raw material:

$$\frac{1459 \times 0.025}{184} / 0.88 \times 100 = 22.5\%$$

(184:molecular weight of HFA.H$_2$O)

Yield based on the introduced ozone:

$$\frac{1459 \times 0.025}{184} / \frac{27.1 \times 504}{48 \times 1000} \times 100 = 69.7\%$$

(48:molecular weight of ozone)

EXAMPLE 2

A stainless steel reactor tube filled with 110 g of calcined activated carbon was heated to the temperature of 200° C., and 150 g (0.45 moles) of octafluoroisobutyl methyl ether (purity: 70%) was passed through the reactor tube from the overhead together with 11 l (0.49 moles) of an oxygen gas for 1.6 hours. The gas leaving the reactor tube was introduced into 100 ml of water in a flask having a capacity of 300 ml and further into a dry ice-methanol trap having a capacity of 500 ml and discharged.

In the water trap (content: 129.2 g), hexafluoroacetone hydrate (HFA.H$_2$O) was formed at a concentration of about 18.9% by weight, as determined according to the F-NMR internal standard method, and likewise 2.95 g of an aqueous layer containing hexafluoroacetone hydrate at a concentration of about 18% by weight was also formed in the dry ice-methanol trap. Besides the aqueous layers, 45.7 g of the raw material was recovered. Separation of the hexafluoroacetone hydrate from the aqueous layers was readily carried out by extraction with an etheral solvent.

Yield based on the raw material:

$$\frac{129.2 \times 0.189 + 2.95 \times 0.18}{184} / 0.45 \times 100 = 30.1\%$$

Yield based on the oxygen:

$$\frac{129.2 \times 0.189 + 2.95 \times 0.18}{184} / 0.49 \times 100 = 27.7\%$$

EXAMPLE 3

Thermal decomposition was carried out in the same manner as in Example 2, except that 150 g (0.61 mole) of heptafluoroisobutenyl methyl ether (purity: 87%) was used in place of the octofluoroisobutyl methy ether and passed through the reactor tube together with 16.4 l (0.73 moles) of an oxygen gas for 2 hours.

After the reaction, hexafluoroacetone hydrate was formed at a concentration about 22.9% by weight in the water trap (content: 121.1 g) and 19.6 g of an aqueous layer containing hexafluoroacetone hydrate at a concentration of about 23% by weight was also formed in the dry ice-methanol trap. Besides the aqueous layers, 14.3 g of the raw material was recovered.

Yield based on the raw material:

$$\frac{121.1 \times 0.229 + 19.6 \times 0.23}{184} / 0.61 \times 100 = 28.7\%$$

Yield based on the oxygen:

$$\frac{121.1 \times 0.229 + 19.6 \times 0.23}{184} / 0.73 \times 100 = 24.0\%$$

EXAMPLE 4

Thermal decomposition was carried out in the same manner as in Example 2, except that 150 g (0.44 moles) of heptafluoroisobutenyl benzyl ether (purity: 85%) was used in place of the heptafluoroisobutyl methyl ether and passed through the reactor tube together with 11.9 l (0.53 moles) of an oxygen gas for 1.7 hours.

After the reaction, hexafluoroacetone hydrate was formed at a concentration of about 18.5% by weight in the water trap (content: 128.0 g) and 2.1 g of an aqueous layer containing hexafluoroacetone hydrate at a concentration of about 19% by weight was formed in the dry ice-methanol trap. Besides the aqueous layers, 58.6 g of the raw material was recovered.

Yield based on the raw material:

$$\frac{128.0 \times 0.185 + 2.1 \times 0.19}{184} / 0.44 \times 100 = 29.7\%$$

Yield based on the oxygen:

$$\frac{128.0 \times 0.185 + 2.1 \times 0.19}{184} / 0.53 \times 100 = 24.7\%$$

What is claimed is:

1. A process for producing hexafluoroacetone or its hydrate which comprises reacting a compound having the formula $(CF_3)_2C=CFOR$ 

wherein R is selected from the group consisting of a $C_1$-$C_{10}$ alkyl group, an aryl group and a benzyl group, with an oxygen-containing gas having an ozone concentration of 2.5 to 400 mg per liter and at a temperature of $-70°$ to $110°$ C.

2. A process according to claim 1 wherein the reaction is carried out at a temperature of $-40°$ to $60°$ C.

3. A process according to claim 1 wherein R is a methyl group.

4. A process according to claim 2 wherein R is a methyl group.

* * * * *